United States Patent
Pedersen et al.

(10) Patent No.: US 11,006,215 B2
(45) Date of Patent: May 11, 2021

(54) HEARING PROTECTION DEVICE WITH MULTIBAND LIMITER AND RELATED METHOD

(71) Applicant: GN Hearing A/S, Ballerup (DK)

(72) Inventors: Søren Christian Voigt Pedersen, Ballerup (DK); Peter Websdell, Ballerup (DK); Peter Rudolph Snoeren, Ballerup (DK)

(73) Assignee: GN Hearing A/S, Ballerup (DK)

( * ) Notice: Subject to any disclaimer, the term of this patent is extended or adjusted under 35 U.S.C. 154(b) by 0 days.

(21) Appl. No.: 16/201,898

(22) Filed: Nov. 27, 2018

(65) Prior Publication Data
US 2019/0200124 A1   Jun. 27, 2019

(30) Foreign Application Priority Data
Dec. 22, 2017  (EP) .................................... 17210312

(51) Int. Cl.
*H04R 3/04*  (2006.01)
*A61F 11/06*  (2006.01)
(Continued)

(52) U.S. Cl.
CPC ............... *H04R 3/04* (2013.01); *A61F 11/06* (2013.01); *G10K 11/1781* (2018.01);
(Continued)

(58) Field of Classification Search
CPC ...... H04R 3/04; H04R 1/1083; H04R 29/001; H04R 2225/43; H04R 2430/03;
(Continued)

(56) References Cited

U.S. PATENT DOCUMENTS 4,843,626 A * 6/1989 Werrbach ............... H03G 9/005
381/106
2006/0140415 A1   6/2006 Haussmann
(Continued)

FOREIGN PATENT DOCUMENTS

WO   WO 2009/050306 A2   4/2009
WO   WO 2009/050306 A3   4/2009

OTHER PUBLICATIONS

Extended European Search Report and search Opinion dated May 28, 2018 for corresponding European patent application No. 17210312.9.

*Primary Examiner* — Ping Lee
(74) *Attorney, Agent, or Firm* — Vista IP Law Group, LLP

(57) ABSTRACT

A hearing protection device includes: a sub-band splitting module configured to divide a first microphone input signal into sub-band signals having a first sub-band signal and a second sub-band signal; an estimator module configured to estimate signal strength parameters of respective sub-band signals, the signal strength parameters having a first signal strength parameter of the first sub-band signal, and a second signal strength parameter of the second sub-band signal; a multiband limiter; and a limiter controller; wherein the limiter controller is configured to determine gain reductions for the sub-band signals of the first microphone input signal, the gain reductions having a first gain reduction and a second gain reduction, and wherein the limiter controller is configured to control the multiband limiter to apply the second gain reduction to the second sub-band signal, wherein the second gain reduction for the second sub-band signal is based on the first signal strength parameter.

18 Claims, 5 Drawing Sheets

(51) Int. Cl.
*H04R 1/10* (2006.01)
*G10K 11/178* (2006.01)
*H03G 3/30* (2006.01)
*H04R 29/00* (2006.01)
*A61F 11/14* (2006.01)

(52) U.S. Cl.
CPC ......... *H03G 3/3005* (2013.01); *H04R 1/1083* (2013.01); *H04R 29/001* (2013.01); *A61F 2011/145* (2013.01); *H04R 2225/43* (2013.01); *H04R 2430/03* (2013.01)

(58) Field of Classification Search
CPC ... H03G 3/3005; G10K 11/1781; A61F 11/06; A61F 2011/145
See application file for complete search history.

(56) References Cited

U.S. PATENT DOCUMENTS

| | | | | |
|---|---|---|---|---|
| 2011/0274284 A1* | 11/2011 | Mulder | ................ | G10K 11/178 381/72 |
| 2013/0103396 A1* | 4/2013 | Swanson | ............... | G10L 21/034 704/225 |
| 2016/0249145 A1* | 8/2016 | Ohl | ...................... | H04R 25/558 |

* cited by examiner

HEARING PROTECTION DEVICE WITH MULTIBAND LIMITER AND RELATED METHOD

RELATED APPLICATION DATA

This application claims priority to, and the benefit of, European Patent Application No. 17210312.9 filed on Dec. 22, 2017. The entire disclosure of the above application is expressly incorporated by reference herein.

FIELD

The present disclosure relates to a hearing protection device with a multiband limiter and related method. In particular, the present disclosure presents a method of operating a hearing protection device.

BACKGROUND

Hearing protection devices have developed from passive hearing protection devices to active hearing protection devices allowing a user to hear and communicate with others when there is no need for hearing protection, i.e. when no loud sounds/noise is present.

SUMMARY

There is a need for devices and methods that are able to limit incoming sounds to a sound pressure level that does not damage the user's hearing or is discomforting to the user while maintaining or increasing speech intelligibility and/or avoiding excessive gain reductions.

Accordingly, a hearing protection device is disclosed, the hearing protection device comprising a first microphone for provision of a first microphone input signal; a sub-band splitting module for dividing the first microphone input signal into a plurality of sub-band signals, an estimator module for estimating a signal strength parameter of respective sub-band signals including a first signal strength parameter of a first sub-band signal and a second signal strength parameter of a second sub-band signal; a multiband limiter configured for applying a gain reduction (filter transfer function) to the first microphone input signal or each of the sub-band signals; and a limiter controller connected to the multiband limiter. The limiter controller is configured to determine gain reductions for the sub-band signals of the first microphone input signal. A second gain reduction for the second sub-band signal is based on the first signal strength parameter for the first sub-band signal, and the limiter controller is configured to control the multiband limiter to apply the second gain reduction to the second sub-band signal or a filter transfer function based on the second gain reduction to the first microphone input signal.

Also disclosed is a method of operating a hearing protection device, the method comprising obtaining a first microphone input signal; dividing the first microphone input signal into a plurality of sub-band signals; estimating a signal strength parameter of respective sub-band signals including a first signal strength parameter of a first sub-band signal and a second signal strength parameter of a second sub-band signal; determining a gain reduction for each sub-band signal of the first microphone input signal, wherein a second gain reduction for the second sub-band signal is based on the first signal strength parameter for the first sub-band signal; and applying the gain reduction to respective sub-band signals.

It is an advantage of the present disclosure that the broadband output signal strength of the hearing protection device is limited to a broadband signal strength limit while gain reduction/attenuation is only applied where essential, in frequency ranges with maximum energy. This is beneficial since, for instance, if a user is communicating in a noisy environment and the speech and interfering noise occupy different frequency ranges, the noise could be reduced while leaving the speech unaffected and thus speech intelligibility could be improved.

Further, the present disclosure provides a broadband output signal strength close to or just below the broadband signal strength limit.

In the method and/or hearing protection device, gain reduction is only performed in the frequency bands/sub-band signals with the highest energy, in which it is essential to reduce the level such that the broad-band power is limited to the Power limit.

A hearing protection device includes: a first microphone for provision of a first microphone input signal; a sub-band splitting module configured to divide the first microphone input signal into a plurality of sub-band signals, the plurality of sub-band signals having a first sub-band signal and a second sub-band signal; an estimator module configured to estimate signal strength parameters of respective sub-band signals, the signal strength parameters having a first signal strength parameter of the first sub-band signal, and a second signal strength parameter of the second sub-band signal; a multiband limiter; and a limiter controller connected to the multiband limiter; wherein the limiter controller is configured to determine gain reductions for the sub-band signals of the first microphone input signal, the gain reductions having a first gain reduction and a second gain reduction, and wherein the limiter controller is configured to control the multiband limiter to apply the second gain reduction to the second sub-band signal, wherein the second gain reduction for the second sub-band signal is based on the first signal strength parameter for the first sub-band signal.

Optionally, the second gain reduction for the second sub-band signal of the first microphone input signal is also based on the second signal strength parameter for the second sub-band signal.

Optionally, the first sub-band signal has a lowest signal strength parameter.

Optionally, the limiter controller is configured to determine one or more of the gain reductions based on a broadband signal strength limit.

Optionally, the limiter controller is configured to determine a signal strength threshold $P\_TH\_2$ for the second sub-band signal based on the broadband signal strength limit.

Optionally, the signal strength threshold $P\_TH\_2$ is given by:

$$P\_TH\_2 = \frac{P_{lim} - P_1}{K - 1}$$

wherein $P_{lim}$ is the broadband signal strength limit, $P_1$ is the first signal strength parameter of the first sub-band signal, and K is a number of the sub-band signals.

Optionally, the limiter controller is configured to determine the second gain reduction based on the signal strength threshold $P\_TH\_2$, in accordance with the signal strength threshold $P\_TH\_2$ satisfying a gain reduction criterion.

Optionally, the limiter controller is configured to determine a third gain reduction for a third sub-band signal of the first microphone input signal, the third sub-band signal having a third signal strength parameter larger than the first signal strength parameter and the second signal strength parameter, and wherein the limiter controller is configured to control the multiband limiter to apply the third gain reduction to the third sub-band signal.

Optionally, the limiter controller is configured to determine the third gain reduction based on a signal strength threshold P_TH_2, in accordance with the signal strength threshold P_TH_2 satisfying a gain reduction criterion.

Optionally, the limiter controller is configured to determine a signal strength threshold P_TH_3 based on a broadband signal strength limit, in accordance with a signal strength threshold P_TH_2 not satisfying a gain reduction criterion.

Optionally, the limiter controller is configured to determine the third gain reduction based on the signal strength threshold P_TH_3, in accordance with the signal strength threshold P_TH_3 satisfying another gain reduction criterion.

Optionally, the signal strength parameters are powers.

A method of operating a hearing protection device, includes: obtaining a first microphone input signal; dividing the first microphone input signal into a plurality of sub-band signals, the sub-band signals having a first sub-band signal and a second sub-band signal; estimating a first signal strength parameter of the first sub-band signal, and a second signal strength parameter of the second sub-band signal; determining gain reductions for the sub-band signals of the first microphone input signal, the gain reductions having a first gain reduction and a second gain reduction, wherein the second gain reduction for the second sub-band signal is based on the first signal strength parameter for the first sub-band signal; and applying the second gain reduction to the second sub-band signal.

Optionally, the act of determining the gains reduction for the sub-band signals of the first microphone input signal comprises: sorting the sub-band signals in ascending signal strength parameter order; initializing an index n; and determining an n'th signal strength threshold P_TH_n based on a broadband signal strength limit.

Optionally, the act of determining the gain reductions for the sub-band signals of the first microphone input signal also comprises: in accordance with the n'th signal strength threshold P_TH_n not satisfying an n'th gain reduction criterion (P_TH_n≤P_n), incrementing the index n and returning to determining an n'th signal strength threshold P_TH_n based on the broadband signal strength limit.

Optionally, the gain reductions for the sub-band signals are determined based on the n'th signal strength threshold, and wherein the gain reductions GR_i are given as P_TH_n/P_i for i=n, . . . , K, K being a number of the sub-band signals, and the gain reductions GR_i for i=1, . . . , n−1 are set to 1.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1A:
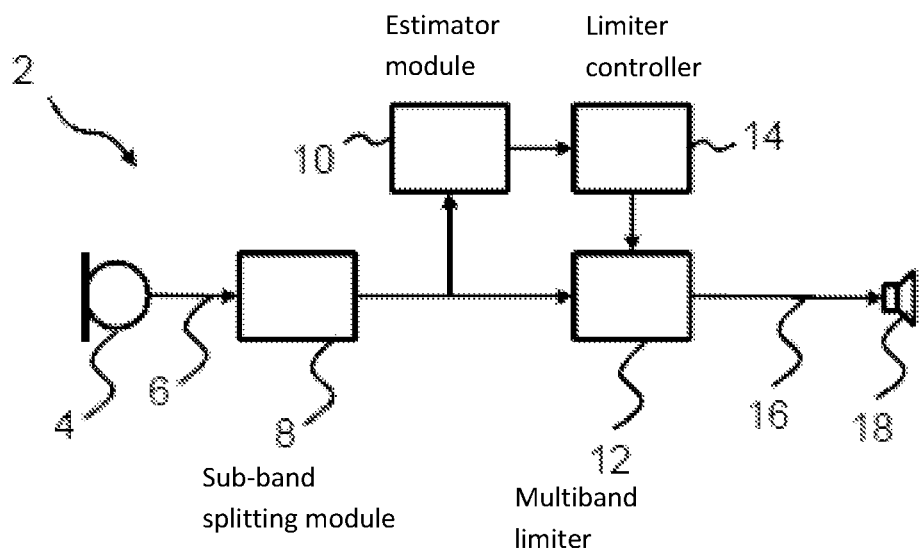
FIG. 1A schematically illustrates an exemplary hearing protection device.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

A hearing protection device is disclosed. A hearing protection device may comprise a housing configured to be at least partly inserted in the ear of a user for blocking the ear canal and/or the pinna to prevent audio from reaching the ear drum.

The hearing protection device comprises a first microphone for provision of a first microphone input signal.

The hearing protection device comprises a sub-band splitting module for dividing the first microphone input signal into K sub-band signals $S^{(1)}, S^{(2)}, \ldots, S^{(K)}$. The sub-band splitting module may be a filter bank or an FFT (Fast Fourier Transform) module. The number K of sub-bands may be three, four, five, six, or at least four. In one or more exemplary hearing protection devices, the number K of sub-bands may be at least eight, such as at least 16. The sub-band signals $S^{(1)}, S^{(2)}, \ldots, S^{(K)}$ are delimited by frequency. The number K of sub-bands may be in the range from 8 to 40.

The hearing protection device comprises an estimator module for estimating signal strength parameters, such as powers or amplitudes, of respective sub-band signals including a first signal strength parameter P_1 of a first sub-band signal S_1 of sub-band signals $S^{(1)}, S^{(2)}, \ldots, S^{(K)}$ and a second signal strength parameter P_2 of a second sub-band signal S_2 of sub-band signals $S^{(1)}, S^{(2)}, \ldots, S^{(K)}$.

The hearing protection device comprises a multiband limiter configured for applying a gain reduction to each of the sub-band signals $S^{(1)}, S^{(2)}, \ldots, S^{(K)}$ or for applying a filter transfer function to the first microphone input signal.

The multiband limiter may comprise a multiplier module for applying a gain reduction to each of the sub-band signals $S^{(1)}, S^{(2)}, \ldots, S^{(K)}$ and a combining module, e.g. including IFFT, for combining the gain reduced sub-band signals from the multiplier module to electrical output signal being fed to the receiver for converting the electrical output signal to an audio output signal.

The hearing protection device may comprise a receiver (loudspeaker) connected to an output of the multiband limiter for converting an electrical output signal to an audio signal.

The hearing protection device may comprise a limiter controller connected to the multiband limiter for controlling the gain reduction applied to the sub-band signals.

The limiter controller may comprise an averaging module. Thus, estimated signal strength parameters can be averaged, and the degree of time averaging can be adjusted to control the speed with which the multiband limiter will react to changes in incoming sounds.

The limiter controller may comprise a gain reduction calculator configured to determine gain reductions for the sub-band signals of the first microphone input signal based on one or more of the signal strength parameters P_1, ..., P_K.

The limiter controller may comprise, e.g. in a time domain implementation, a filter design module configured to determine a filter transfer function/filter coefficients for the multiband limiter 12 implemented as a FIR filter.

The limiter controller may comprise a threshold module 14D for determining signal strength thresholds for the gain reduction calculator.

The limiter controller is configured to determine gain reductions $GR^{(1)}, GR^{(2)}, \ldots, GR^{(K)}$ for the sub-band signals $S^{(1)}, S^{(2)}, \ldots, S^{(K)}$ of the first microphone input signal and optionally determine a filter transfer function (filter coefficients) for a filter, e.g. a FIR filter of the multiband limiter.

A second gain reduction GR_2 for the second sub-band signal S_2 is based on the first signal strength parameter P_1 for the first sub-band signal S_1. The second gain reduction GR_2 for the second sub-band signal S_2 of the first microphone input signal may be based on the second signal strength parameter P_2 for the second sub-band signal.

The limiter controller is configured to control the multiband limiter to apply the second gain reduction GR_2 to the second sub-band signal S_2 of sub-band signals $S^{(1)}, S^{(2)}, \ldots, S^{(K)}$.

The first sub-band signal S_1 is the sub-band signal of sub-band signals $S^{(1)}, S^{(2)}, \ldots, S^{(K)}$ with the lowest signal strength parameter, e.g. the sub-band signal $S^{(1)}, S^{(2)}, \ldots, S^{(K)}$ with the lowest power or amplitude.

The second sub-band signal S_2 is the sub-band signal of sub-band signals $S^{(1)}, S^{(2)}, \ldots, S^{(K)}$ with the second-lowest signal strength parameter, e.g. the sub-band signal $S^{(1)}, S^{(2)}, \ldots, S^{(K)}$ with the second-lowest power or amplitude.

The n'th sub-band signal S_n is the sub-band signal of sub-band signals $S^{(1)}, S^{(2)}, \ldots, S^{(K)}$ with the n'th-lowest signal strength parameter, e.g. the sub-band signal $S^{(1)}, S^{(2)}, \ldots, S^{(K)}$ with the n'th-lowest power or amplitude.

The limiter controller is optionally configured to sort the sub-band signals $S^{(1)}, S^{(2)}, \ldots, S^{(K)}$ into a sorted list of sub-band signals S_1, S_2, ..., S_K in ascending signal strength parameter order.

The limiter controller is optionally configured to control the multiband limiter to apply the gain reductions GR_n to the n'th sub-band signal S_n of sub-band signals $S^{(1)}, S^{(2)}, \ldots, S^{(K)}$ wherein n=1, ..., K.

To determine gain reductions for the sub-band signals of the first microphone input signal may be based on a broadband signal strength limit Rim. The broadband signal strength limit $P_{lim}$ may be a broadband power limit or a broadband amplitude limit. The power limit $P_{lim}$ is the broad-band power which the first microphone input signal should not exceed. This level may equate to a sound pressure level at the first microphone and will typically be taken from occupational health standards (e.g. EU Directive 2003/10/EC-noise) and may be a frequency-weighted value (e.g. A-weighted) or un-weighted level.

To determine gain reductions for the sub-band signals of the first microphone input signal may comprise to determine a second signal strength threshold P_TH_2 for the second sub-band signal S_2, e.g. based on the broadband signal strength limit $P_{lim}$.

In one or more exemplary hearing protection devices, to determine gain reductions for the sub-band signals of the first microphone input signal comprises to determine a first signal strength threshold P_TH_1 for the first sub-band signal based on the broadband signal strength limit $Pl_{im}$, and in accordance with the first signal strength threshold P_TH_1 satisfying a first gain reduction criterion, e.g. P_1≥P_TH_1, determining the gain reductions based on the first signal strength threshold, e.g. GR_i=P_TH_1/P_i for i=1, ..., K.

The first signal strength threshold P_TH_1 may be given by:

$$P\_TH\_1 = \frac{P_{lim}}{K}$$

Signal strength thresholds may be power thresholds or amplitude thresholds.

The second signal strength threshold P_TH_2 may be given by:

$$P\_TH\_2 = \frac{P_{lim} - P_1}{K - 1}$$

wherein $P_{lim}$ is the broadband signal strength limit, $P_1$ is the signal strength parameter of the first sub-band signal S_1, K is the number of sub-band signals and k is an index.

To determine gain reductions for the sub-band signals of the first microphone input signal may comprise, in accordance with the second signal strength threshold P_TH_2 satisfying a second gain reduction criterion, e.g. P_2≥P_TH_2, determining the second gain reduction GR_2 based on the second signal strength threshold P_TH_2. The second gain reduction GR_2 may be given as:

*GR_2=P_TH_2/P_2*

To determine gain reductions for the sub-band signals of the first microphone input signal may comprise, in accordance with the n'th signal strength threshold P_TH_n satisfying an n'th gain reduction criterion, setting the gain reductions GR_1-GR_n−1 to one (1).

To determine gain reductions for the sub-band signals of the first microphone input signal may comprise to determine a third gain reduction GR_3 for a third sub-band signal S_3 of sub-band signals $S^{(1)}, S^{(2)}, \ldots, S^{(K)}$, the third sub-band signal S_3 having a third signal strength parameter P_3 larger than the first signal strength parameter P_1 and larger than the second signal strength parameter P_2, and wherein the limiter controller is configured to control the multiband limiter to apply the third gain reduction GR_3 to the third sub-band signal S_3 of sub-band signals $S^{(1)}, S^{(2)}, \ldots, S^{(K)}$.

To determine gain reductions for the sub-band signals of the first microphone input signal may comprise, in accordance with the second signal strength threshold P_TH_2 satisfying the second gain reduction criterion, determining the third gain reduction based on the second signal strength threshold, wherein the third gain reduction GR_3 may be given as:

*GR_3=P_TH_2/P_3*

To determine gain reductions for the sub-band signals of the first microphone input signal may comprise, in accordance with the second signal strength threshold P_TH_2 satisfying a second gain reduction criterion, e.g. P_2≥P_TH_2, determining the gain reductions GR_2-GR_K as:

GR_i=P_TH_2/P_i for i=2, . . . ,K.

To determine gain reductions for the sub-band signals of the first microphone input signal may comprise, in accordance with the second signal strength threshold P_TH_2 not satisfying the second gain reduction criterion, to determine a third signal strength threshold P_TH_3 based on the broadband signal strength limit $P_{lim}$.

The third signal strength threshold P_TH_3 may be given by:

$$P\_TH\_3 = \frac{P_{lim} - \sum_{k=1}^{2} P_k}{K - 2}$$

wherein $P_{lim}$ is the broadband signal strength limit, $P_k$ is the signal strength parameter of the k'th sub-band signal, K is the number of sub-band signals and k is an index.

To determine gain reductions for the sub-band signals of the first microphone input signal may comprise, in accordance with the third signal strength threshold P_TH_3 satisfying a third gain reduction criterion, e.g. P_3≥P_TH_3, determining the third gain reduction GR_3 based on the third signal strength threshold P_TH_3. The third gain reduction GR_3 may be given as:

GR_3=P_TH_3/P_3

To determine gain reductions for the sub-band signals of the first microphone input signal may comprise, in accordance with the third signal strength threshold P_TH_3 satisfying a third gain reduction criterion, e.g. P_3≥P_TH_3, determining the gain reductions GR_3-GR_K as:

GR_i=P_TH_3/P_i for i=3, . . . ,K.

The method of operating a hearing protection device comprises obtaining a first microphone input signal, e.g. with first microphone; dividing the first microphone signal into a plurality of K sub-band signals $S^{(1)}, S^{(2)}, \ldots, S^{(K)}$; and estimating signal strength parameters, such as powers or amplitudes of respective sub-band signals including a first signal strength parameter P_1 of a first sub-band signal S_1 and a second signal strength parameter P_2 of a second sub-band signal S_2. The method comprises determining a gain reduction for each sub-band signal $S^{(1)}, S^{(2)}, \ldots, S^{(K)}$ of the first microphone input signal, wherein a second gain reduction GR_2 for the second sub-band signal S_2 of sub-band signals $S^{(1)}, S^{(2)}, \ldots, S^{(K)}$ is based on the first signal strength parameter P_1 for the first sub-band signal S_1; and applying the gain reduction to respective sub-band signals $S^{(1)}, S^{(2)}, \ldots, S^{(K)}$ or to the first microphone input signal, e.g. to form an electrical output signal. The method may comprise converting the electrical output signal to an audio signal, e.g. with a receiver of the hearing protection device.

In the method, determining a gain reduction for each sub-band signal $S^{(1)}, S^{(2)}, \ldots, S^{(K)}$ of the first microphone input signal may comprise sorting the sub-band signals $S^{(1)}, S^{(2)}, \ldots, S^{(K)}$ in a list of sub-band signals S_1, S_2, . . . , S_K in ascending signal strength parameter order.

In the method, determining a gain reduction for each sub-band signal $S^{(1)}, S^{(2)}, \ldots, S^{(K)}$ of the first microphone input signal may comprise: initializing an index n, determining an n'th signal strength threshold P_TH_n based on broadband signal strength limit and in accordance with the n'th signal strength threshold P_TH_n not satisfying an n'th gain reduction criterion (P_TH_n≤P_n), incrementing the index n and returning to determining an n'th signal strength threshold P_TH_n based on broadband signal strength limit. The method may comprise, in accordance with the n'th signal strength threshold P_TH_n satisfying an n'th gain reduction criterion, determining the gain reductions GR_i for i=n, . . . , K based on the n'th signal strength threshold. The gain reductions GR_i may be given as P_TH_n/P_i for i=n, . . . , K.

In accordance with the n'th signal strength threshold P_TH_n satisfying an n'th gain reduction criterion, the gain reductions GR_i for i=1, . . . , n−1 may be set to 1.

Determining an n'th a signal strength threshold P_TH_n may be based on one or more signal strength parameters P_k, for k=1, . . . , n−1, i.e. on one or more signal strength parameters of sub-band signals with lower signal strength parameter than the n'th signal strength parameter.

The n'th signal strength threshold may be given as:

$$P\_TH\_n = \frac{P_{lim} - \sum_{k=1}^{n-1} P_k}{K - (n-1)}$$

wherein $P_{lim}$ is a broadband signal strength limit, P_k is the signal strength parameter of the k'th sub-band signal, K is the number of sub-band signals and k is an index.

FIG. 1A shows an exemplary hearing protection device. The hearing protection device 2 comprises a first microphone 4 for provision of a first microphone input signal 6; a sub-band splitting module 8 for dividing the first microphone signal 6 into K sub-band signals; and an estimator module 10 for estimating signal strength parameters of respective sub-band signals $S^{(1)}, S^{(2)}, \ldots, S^{(K)}$ including a first signal strength parameter P_1 of a first sub-band signal $S_1$ and a second signal strength parameter P_2 of a second sub-band signal S_2 of the sub-band signals $S^{(1)}, S^{(2)}, \ldots, S^{(K)}$. The hearing protection device 2 comprises a multiband limiter 12 configured for applying a gain reduction to each of the sub-band signals $S^{(1)}, S^{(2)}, \ldots, S^{(K)}$; and a limiter controller 14 connected to the multiband 12.

The limiter controller 14 is configured to determine gain reductions for the sub-band signals of the first microphone input signal, wherein a second gain reduction $GR_2$ for the second sub-band signal S_2 of sub-band signals $S^{(1)}, S^{(2)}, \ldots, S^{(K)}$ is based on the first signal strength parameter P_1 for the first sub-band signal S_1. The limiter controller 14 is configured to control the multiband limiter 12 to apply the second gain reduction GR_2 to the second sub-band signal S_2, i.e. to the sub-band signal with the second lowest signal strength parameter of sub-band signals $S^{(1)}, S^{(2)}, \ldots, S^{(K)}$. The multiband limiter 12 feeds an electric output signal 16 to receiver 18 for converting the electrical output signal 16 to an audio output signal. The limiter controller 14 is configured to control the multiband limiter 12 to apply the gain reductions GR_1, GR_K to respective sub-band signals S_1, S_2, . . . , S_K.

Figure 1B:
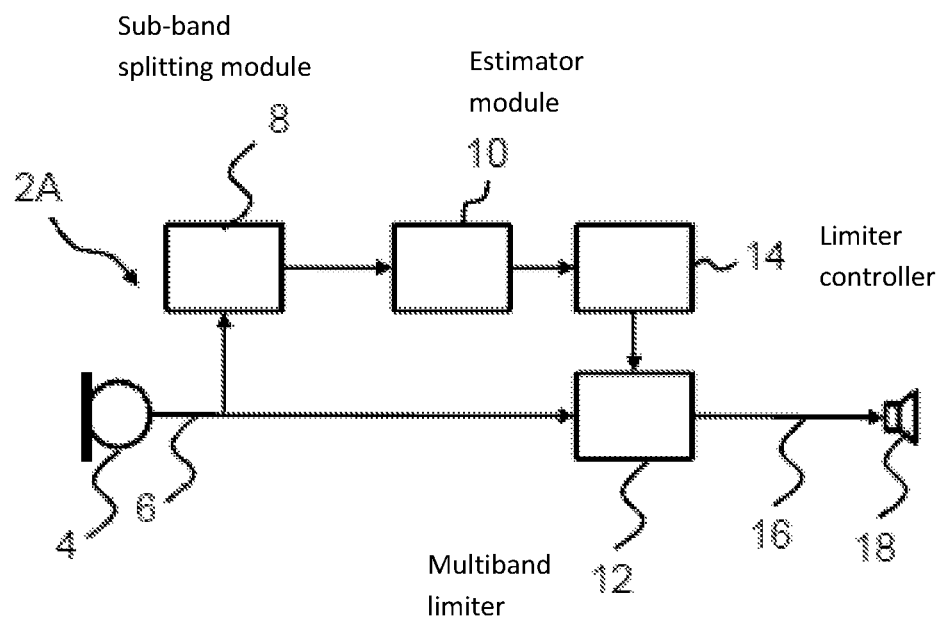
FIG. 1B schematically illustrates an exemplary hearing protection device.

FIG. 1B shows an exemplary hearing protection device. The hearing protection device 2B comprises a first microphone 4 for provision of a first microphone input signal 6; a sub-band splitting module 8 for dividing the first microphone signal 6 into K sub-band signals; and an estimator module 10 for estimating signal strength parameters of respective sub-band signals $S^{(1)}, S^{(2)}, \ldots, S^{(K)}$ including a first signal strength parameter P_1 of a first sub-band signal $S_1$ and a second signal strength parameter P_2 of a second sub-band signal S_2 of the sub-band signals $S^{(1)}, S^{(2)}, \ldots, S^{(K)}$ The hearing protection device 2A comprises a multi-band limiter 12 configured for applying gain reduction the first microphone input signal; and a limiter controller 14 connected to the multiband limiter 12.

The limiter controller 14 is configured to determine gain reductions for the sub-band signals of the first microphone input signal, wherein a second gain reduction for the second sub-band signal is based on the first signal strength parameter for the first sub-band signal, and wherein the limiter controller is configured to determine and apply gain reduction for the first microphone input signal as a filter transfer function for multiband limiter 12 based on at least the second gain reduction, such as all gain reductions of sub-band signals $S^{(1)}, S^{(2)}, \ldots, S^{(K)}$ The limiter controller 14 is configured to control the multiband limiter 12 to apply the filter transfer function to the microphone input signal 6. The multiband limiter 12 feeds an electric output signal 16 to receiver 18 for converting the electrical output signal 16 to an audio output signal.

Figure 2:
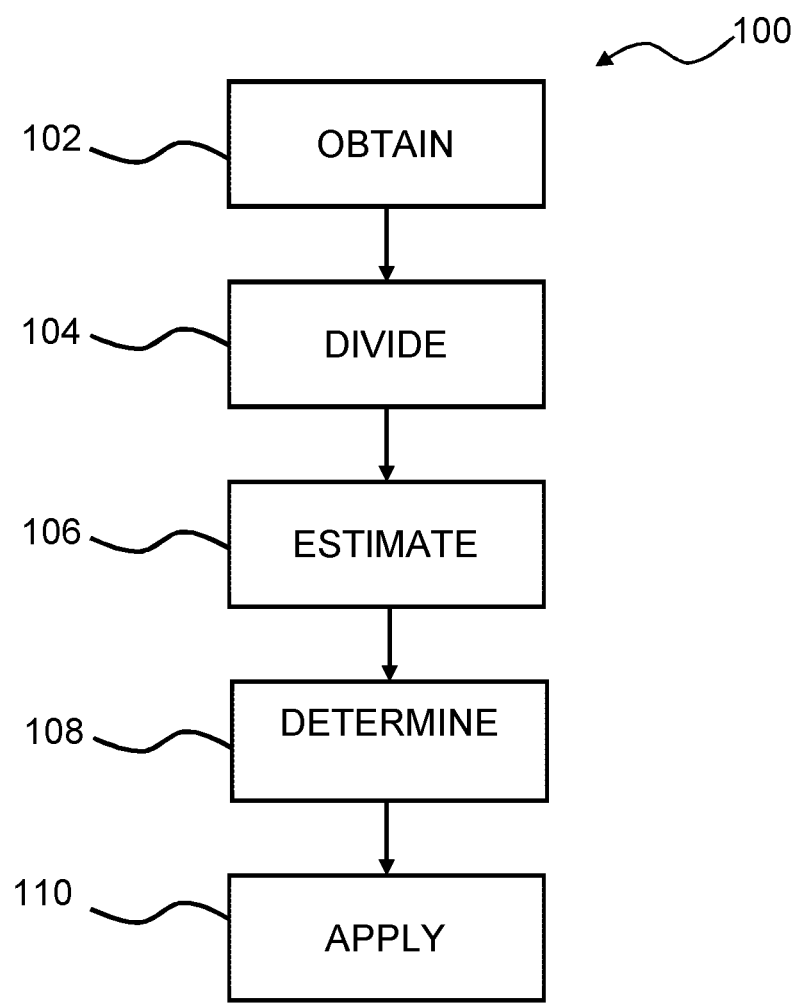
FIG. 2 is a flowchart of an exemplary method.

FIG. 2 shows a flow diagram of an exemplary method of operating a hearing protection device. The method 100 comprises obtaining 102 a first microphone input signal; dividing 104 the first microphone input signal into a plurality of sub-band signals; estimating 106 a signal strength parameter of respective sub-band signals including a first signal strength parameter of a first sub-band signal and a second signal strength parameter of a second sub-band signal; determining 108 a gain reduction for each sub-band signal of the first microphone input signal, wherein a second gain reduction for the second sub-band signal is based on the first signal strength parameter for the first sub-band signal; and applying 110 the gain reduction to respective sub-band signals.

Figure 3:
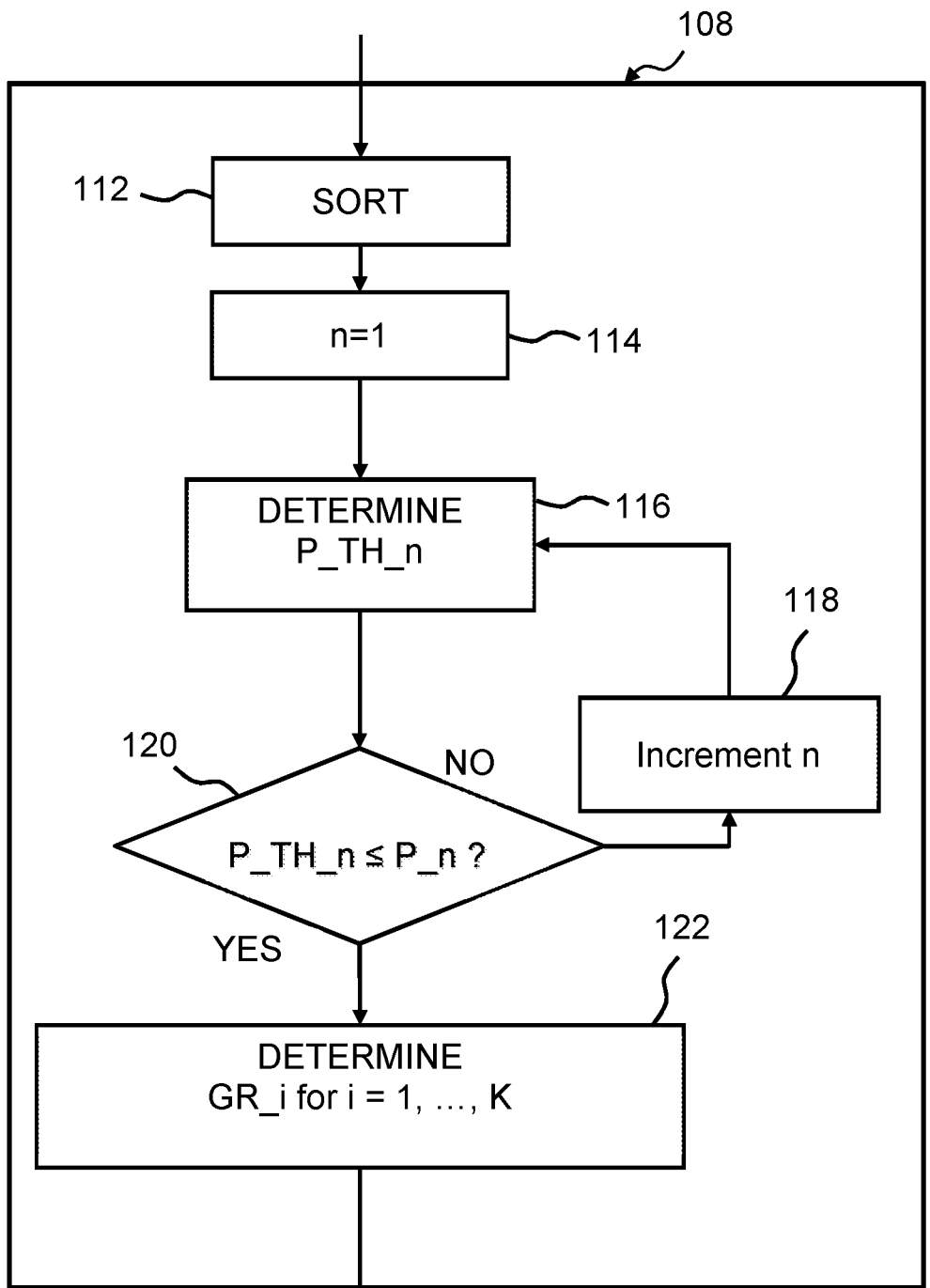
FIG. 3 shows a part of an exemplary method.

FIG. 3 illustrates an example of determining 108 a gain reduction for each sub-band signal of the first microphone input signal. 108 a gain reduction for each sub-band signal $S^{(1)}, S^{(2)}, \ldots, S^{(K)}$ of the first microphone input signal comprises sorting 112 the sub-band signals $S^{(1)}, S^{(2)}, \ldots, S^{(K)}$ in a list of sub-band signals S_1, S_2, . . . , S_K in ascending signal strength parameter order. Further, determining 108 a gain reduction for each sub-band signal $S^{(1)}, S^{(2)}, \ldots, S^{(K)}$ of the first microphone input signal comprises: 114 an index n; determining 116 an n'th a signal strength threshold P_TH_n based on broadband signal strength limit; and in accordance with the n'th signal strength threshold P_TH_n not satisfying an n'th gain reduction criterion (P_TH_n≤P_n), incrementing 118 the index n and returning to determining 116 an n'th signal strength threshold P_TH_n based on broadband signal strength limit. Thus, 108 comprises determining 120 if the n'th a signal strength threshold P_TH_n satisfies an n'th gain criterion. In accordance with the n'th signal strength threshold P_TH_n satisfying the n'th gain reduction criterion, determining 108 comprises determining 122 the gain reductions GR_i for i=1, . . . , K. Determining 122 comprises determining the gain reductions GR_i for i=n, K based on the n'th signal strength threshold, gain reductions GR_i are given as P_TH_n/P_i for i=n, K, and the gain reductions GR_i for i=1, . . . , n−1 are set to 1.

The n'th signal strength threshold is given as:

$$P\_TH\_n = \frac{P_{lim} - \sum_{k=1}^{n-1} P_k}{K - (n-1)}$$

wherein $P_{lim}$ is a broadband signal strength limit, $P_k$ is the signal strength parameter of the k'th sub-band signal, K is the number of sub-band signals and k is an index.

Figure 4:
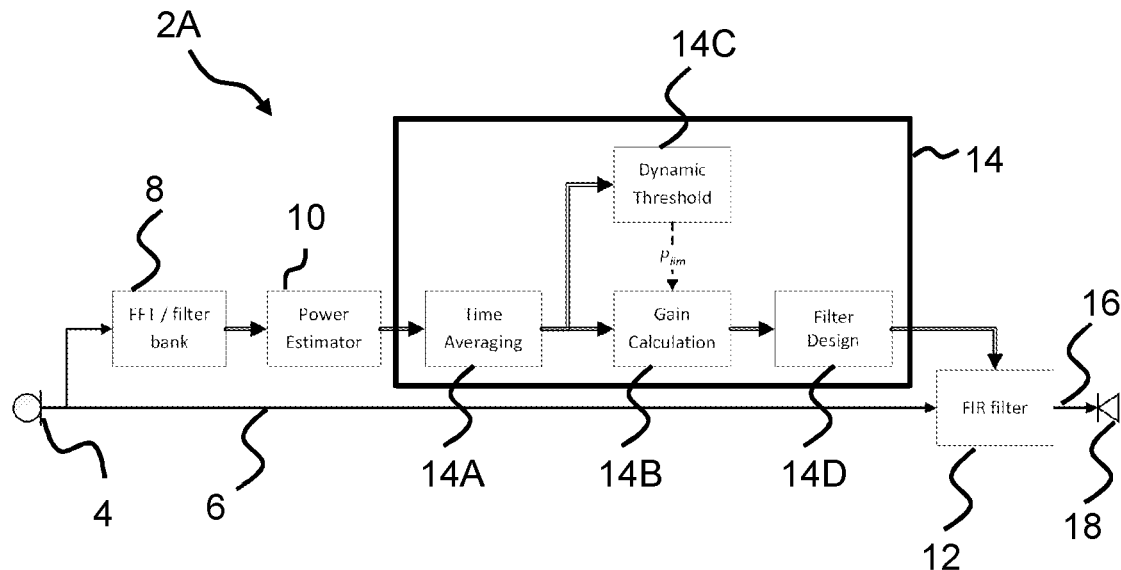
FIG. 4 schematically illustrates an exemplary hearing protection device.

FIG. 4 shows an exemplary time domain implementation of hearing protection device 2A in FIG. 1B. The sub-band splitting module 8 comprises a filter bank or an FFT (Fast Fourier Transform) module for dividing the first microphone signal 6 into K sub-band signals $S^{(1)}, S^{(2)}, \ldots, S^{(K)}$ that are fed to the estimator module 10. The estimator module 10 is a power estimator and estimates a power of respective sub-band signals $S^{(1)}, S^{(2)}, \ldots, S^{(K)}$ including a first power P_1 of a first sub-band signal $S_1$ and a second power P_2 of a second sub-band signal S_2 of the sub-band signals $S^{(1)}, S^{(2)}, \ldots, S^{(K)}$. The hearing protection device 2 comprises a multiband limiter 12 being a FIR filter configured for applying a filter transfer function to the first microphone input signal 6.

The limiter controller 14 comprises averaging module 14A and gain reduction calculator 14B configured to determine gain reductions for the sub-band signals of the first microphone input signal, wherein a second gain reduction $GR_2$ for the second sub-band signal S_2 of sub-band signals $S^{(1)}, S^{(2)}, \ldots, S^{(K)}$ is based on the first signal strength parameter P_1 for the first sub-band signal S_1. The limiter controller 14 comprises filter design module 14D configured to determine a filter transfer function for the multiband limiter 12 implemented as a FIR filter, and threshold module 14C for determining signal strength thresholds. The limiter controller 14 controls the multiband limiter 12 to apply the filter transfer function to the first microphone input 6. The multiband limiter 12 feeds an electric output signal 16 to receiver 18 for converting the electrical output 16 to an audio output signal.

Figure 5:
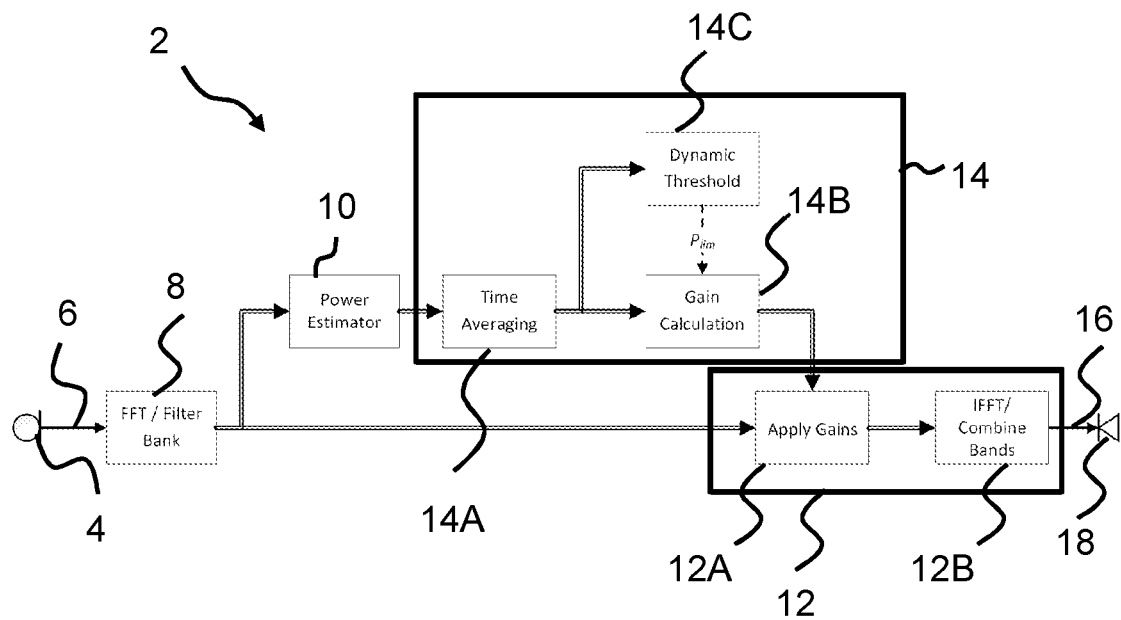
FIG. 5 schematically illustrates an exemplary hearing protection device.

FIG. 5 shows an exemplary frequency domain implementation of hearing protection device 2 in FIG. 1. The sub-band splitting module 8 comprises a filter bank or an FFT (Fast Fourier Transform) module for dividing the first microphone signal 6 into K sub-band signals $S^{(1)}, S^{(2)}, \ldots, S^{(K)}$ that are fed to the estimator module 10. The estimator module 10 is a power estimator and estimates a power of respective sub-band signals $S^{(1)}, S^{(2)}, \ldots, S^{(K)}$ including a first power P_1 of a first sub-band signal $S_1$ and a second power P_2 of a second sub-band signal S_2 of the sub-band signals $S^{(1)}, S^{(2)}, \ldots, S^{(K)}$. The hearing protection device 2 comprises a multiband limiter 12 with a multiplier module 12A for applying a gain reduction to each of the sub-band signals $S^{(1)}, S^{(2)}, \ldots, S^{(K)}$ and a combining module 12B (IFFT) for combining the gain reduced sub-band signals to electrical output signal 16 being fed to receiver 18 for converting the electrical output signal 16 to an audio output signal.

The limiter controller 14 comprises averaging module 14A and gain reduction calculator 14B configured to determine gain reductions for the sub-band signals of the first microphone input signal, wherein a second gain reduction $GR_2$ for the second sub-band signal S_2 of sub-band signals $S^{(1)}, S^{(2)}, \ldots, S^{(K)}$ is based on the first signal strength parameter P_1 for the first sub-band signal S_1. The limiter controller 14 comprises threshold module 14C for determining signal strength thresholds.

The limiter controller 14 is configured to control the multiband limiter 12 to apply the gain reductions GR_1, GR_K to respective sub-band signals S_1, S_2, ..., S_K.

Figure 6:
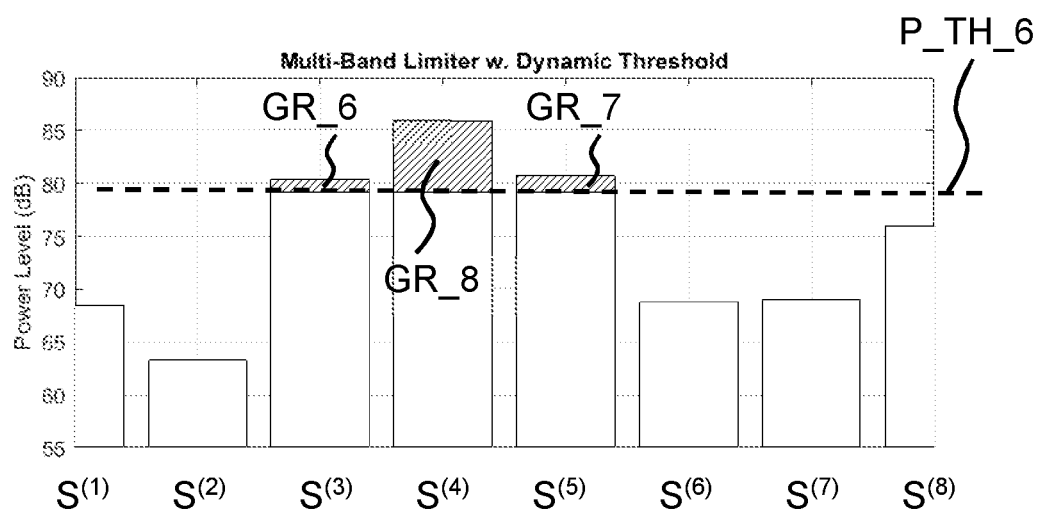
FIG. 6 illustrates multiband limiting of an exemplary monitor device.

FIG. 6 illustrates multiband limiting of an exemplary monitor device/method. A first microphone input signal has been divided into eight sub-band signals $S^{(1)}, S^{(2)}, \ldots, S^{(8)}$ in 8 frequency bands, i.e. K=8. A signal strength parameter (power level) of respective sub-band signals including a first signal strength parameter P_1 of a first sub-band signal S_1 with the lowest signal strength parameter of sub-band signals $S^{(1)}, S^{(2)}, \ldots, S^{(8)}$ and a second signal strength parameter P_1 of a second sub-band signal S_2 with the second-lowest signal strength parameter of sub-band signals $S^{(1)}, S^{(2)}, \ldots, S^{(8)}$.

Table 1 below shows values power values for the multiband limiting of FIG. 6.

TABLE 1

| | S_1 | S_2 | S_3 | S_4 | S_5 | S_6 | S_7 | S_8 |
|---|---|---|---|---|---|---|---|---|
| P_i (dB) | 63.3 | 68.4 | 68.8 | 69.0 | 76.0 | 80.4 | 80.8 | 85.8 |
| GR_i (dB) | 0.0 | 0.0 | 0.0 | 0.0 | 0.0 | −1.2 | −1.6 | −6.6 |
| Mapped sub-band signal | $S^{(2)}$ | $S^{(1)}$ | $S^{(6)}$ | $S^{(7)}$ | $S^{(8)}$ | $S^{(3)}$ | $S^{(5)}$ | $S^{(4)}$ |
| Output power of mapped sub-band signal (dB) | 63.3 | 68.4 | 68.8 | 69.0 | 76.0 | 78.2 | 78.2 | 78.2 |

In this example, power thresholds P_TH_1, P_TH_2, P_TH_3, P_TH_4, and P_TH_5 do not satisfy a respective gain reduction criterion, and the gain reductions GR_1, GR_2, GR_3, GR_4, and GR_5 are set to 1 (0 dB). The hearing protection device has calculated a sixth power threshold P_TH_6=78.2 dB as described herein, and the gain reductions GR_6, GR_7, and GR_8 are set to limit the output of the respective sub-band signal to the sixth power threshold (78.2 dB) in accordance with the sixth power threshold satisfying the sixth gain reduction criterion (P_TH_6≤P_6). The limiter controller controls the multiband limiter to apply the gain reductions to the corresponding sub-band signals to limit the output power of mapped sub-band signals. Accordingly, the first gain reduction GR_1 is applied to $S^{(2)}$ ($S^{(2)}$ being the sub-band signal with the lowest power), the second gain reduction GR_2 is applied to $S^{(1)}$ ($S^{(1)}$ being the sub-band signal with the second-lowest power), the third gain reduction GR_3 is applied to $S^{(6)}$ ($S^{(6)}$ being the sub-band signal with the third-lowest power), the fourth gain reduction GR_4 is applied to $S^{(7)}$ ($S^{(17)}$ being the sub-band signal with the fourth-lowest power), the fifth gain reduction GR_5 is applied to $S^{(8)}$ ($S^{(8)}$ being the sub-band signal with the fifth-lowest power), the sixth gain reduction GR_6 is applied to $S^{(3)}$ ($S^{(3)}$ being the sub-band signal with the sixth-lowest power), the seventh gain reduction GR_7 is applied to $S^{(5)}$ ($S^{(5)}$ being the sub-band signal with the seventh-lowest power), and the eighth gain reduction GR_8 is applied to $S^{(4)}$ ($S^{(4)}$ being the sub-band signal with the eighth-lowest power). In one or more exemplary hearing protection devices, the limiter controller is configured to design a filter transfer function/filter coefficients based on the gain reductions GR_1-GR_8 and apply the filter transfer function/filter coefficients in a filter of the multiband limiter operating on the first microphone input signal.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 2 hearing protection device
4 first microphone
6 first microphone input signal
8 sub-band splitting module
10 estimator module
12 multiband limiter
12A multiplier module
12B combining module
14 limiter controller
14A averaging module
14B gain reduction calculator
14C filter design module
14D threshold module
16 electrical output signal
18 receiver
100 method of operating a hearing protection device
102 obtaining a first microphone input signal;
104 dividing the first microphone signal into a plurality of sub-band signals
106 estimating signal strength parameters
108 determining a gain reduction for each sub-band signal
110 applying the gain reduction to respective sub-band signals
112 sorting sub-band signals
114 initializing an index n
116 determining an n'th signal strength threshold P_TH_n
118 incrementing the index n
120 determining if P_TH_n satisfies n'th gain criterion
122 determining gain reductions GR_i for i=1, ..., K

The invention claimed is:

1. A hearing protection device comprising:
a microphone for provision of a microphone input signal; and
a processing unit comprising a sub-band splitting module configured to divide the microphone input signal into a plurality of sub-band signals;
wherein the processing unit is configured to determine signal strength parameters for the sub-band signals respectively;
wherein the processing unit is configured to determine signal strength thresholds for the sub-band signals respectively based on a broadband signal strength limit;
wherein the processing unit is configured to compare the signal strength parameters respectively with the signal strength thresholds;
wherein the processing unit is configured to determine a gain reduction for one of the sub-band signals, wherein the processing unit is configured to perform a computation using the signal strength threshold for the one of the sub-band signals when determining the gain reduction for the one of the sub-band signals;
wherein the one of the sub-band signals comprises a first sub-band signal;
wherein the processing unit is configured to determine the signal strength threshold for the first sub-band signal based on the broadband signal strength limit and K, wherein K is a number of the sub-band signals;

wherein the processing unit is configured to determine the signal strength threshold for the first sub-band signal based on a relation: $P\_TH\_1 = P_{lim}/K$;

wherein $P\_TH\_1$ is the signal strength threshold for the first sub-band signal, and $P_{lim}$ is the broadband signal strength limit;

wherein the gain reduction is for the first sub-band signal, wherein the signal strength parameters comprise a first signal strength parameter for the first sub-band signal, and wherein the processing unit is configured to determine the gain reduction for the first sub-band signal by using the first signal strength parameter in the computation;

wherein the sub-band signals comprise a second sub-band signal;

wherein the processing unit is configured to determine the signal strength threshold for the second sub-band signal based on a relation: $P\_TH\_2 = (P_{lim} - P_1)/(K-1)$; and wherein $P\_TH\_2$ is the signal strength threshold for the second sub-band signal, and $P_1$ is the signal strength parameter for the first sub-band signal.

2. The hearing protection device according to claim 1, wherein the signal strength parameters are powers.

3. The hearing protection device according to claim 1, wherein the sub-band signals comprise a third sub-band signal;

wherein the processing unit is configured to determine the signal strength threshold for the third sub-band signal based on a relation: $P\_TH\_3 = (P_{lim} - P_1 - P_2)/(K-2)$; and wherein $P\_TH\_3$ is the signal strength threshold for the third sub-band signal, and $P_2$ is the signal strength parameter for the second sub-band signal.

4. The hearing protection device according to claim 1, wherein the hearing protection device is configured to reduce respective powers with different respective power levels for first ones of the sub-band signals to a same level.

5. The hearing protection device according to claim 4, wherein the hearing protection device is configured to keep power levels for second ones of the sub-band signals as unchanged.

6. The hearing protection device according to claim 5, wherein for the first ones of the sub-band signals for which the respective powers are reduced to the same level, the signal strength parameters respectively for the first ones of the sub-band signals are respectively above the signal strength thresholds respectively for the first ones of the sub-band signals.

7. The hearing protection device according to claim 6, wherein for the second ones of the sub-band signals remaining unchanged, the signal strength parameters respectively for the second ones of the sub-band signals are respectively below the signal strength thresholds respectively for the second ones of the sub-band signals.

8. A method performed by a hearing protection device, the method comprising:
obtaining a microphone input signal;
dividing the microphone input signal into a plurality of sub-band signals;
determining signal strength parameters for the sub-band signals respectively;
determining signal strength thresholds for the sub-band signals respectively based on a broadband signal strength limit;
comparing the signal strength parameters respectively with the signal strength thresholds; and
determining a gain reduction for one of the sub-band signals, wherein the act of determining the gain reduction comprises performing a computation using the signal strength threshold for the one of the sub-band signals;

wherein the one of the sub-band signals comprises a first sub-band signal;

wherein the signal strength threshold for the first sub-band signal is determined based on the broadband signal strength limit and K, wherein K is a number of the sub-band signals;

wherein the signal strength threshold for the first sub-band signal is determined based on a relation: $P\_TH\_1 = P_{lim}/K$;

wherein $P\_TH\_1$ is the signal strength threshold for the first sub-band signal, and $P_{lim}$ is the broadband signal strength limit;

wherein the gain reduction is determined for the first sub-band signal, wherein the signal strength parameters comprise a first signal strength parameter for the first sub-band signal, and wherein the act of determining the gain reduction for the first sub-band signal comprises using the first signal strength parameter in the computation;

wherein the sub-band signals comprise a second sub-band signal;

wherein the signal strength threshold for the second sub-band signal is determined based on a relation: $P\_TH\_2 = (P_{lim} - P_1)/(K-1)$; and wherein $P\_TH\_2$ is the signal strength threshold for the second sub-band signal, and $P_1$ is the signal strength parameter for the first sub-band signal.

9. The method according to claim 8, wherein the sub-band signals comprise a third sub-band signal;

wherein the signal strength threshold for the third sub-band signal is determined based on a relation: $P\_TH\_3 = (P_{lim} - P_1 - P_2)/(K-2)$; and wherein $P\_TH\_3$ is the signal strength threshold for the third sub-band signal, and $P_2$ is the signal strength parameter for the second sub-band signal.

10. The method according to claim 8, wherein the act of determining the gain reduction for the one of the sub-band signals is performed in accordance with a processing scheme, and wherein the processing scheme is utilized by the hearing protection device to reduce powers with different respective power levels for first ones of the sub-band signals to a same level.

11. The method according to claim 10, further comprising keeping power levels for second ones of the sub-band signals as unchanged.

12. The method according to claim 11, wherein for the first ones of the sub-band signals for which the respective powers are reduced to the same level, the signal strength parameters respectively for the first ones of the sub-band signals are respectively above the signal strength thresholds respectively for the first ones of the sub-band signals.

13. The method according to claim 12, wherein for the second ones of the sub-band signals remaining unchanged, the signal strength parameters respectively for the second ones of the sub-band signals are respectively below the signal strength thresholds respectively for the second ones of the sub-band signals.

14. A hearing protection device comprising:
a microphone for provision of a microphone input signal; and a processing unit comprising a sub-band splitting module configured to divide the microphone input signal into a plurality of sub-band signals;

wherein the processing unit is configured to determine thresholds respectively for the sub-band signals, determine signal strength parameters respectively for the sub-band signals, and perform comparisons between the signal strength parameters and the respective thresholds;

wherein the hearing protection device is configured to reduce powers with different respective power levels for first ones of the sub-band signals to a same level;

wherein the sub-band signals comprise a first sub-band signal;

wherein the processing unit is configured to determine the threshold for the first sub-band signal based on a broadband signal strength limit and K, wherein K is a number of the sub-band signals wherein the processing unit is configured to determine the threshold for the first sub-band signal based on a relation: $P\_TH\_1 = P_{lim}/K$;

wherein $P\_TH\_1$ is the threshold for the first sub-band signal, and $P_{lim}$ is the broadband signal strength limit;

wherein the gain reduction is for the first sub-band signal, wherein the signal strength parameters comprise a first signal strength parameter for the first sub-band signal, and wherein the processing unit is configured to determine the gain reduction for the first sub-band signal by using the first signal strength parameter in the computation; and wherein the sub-band signals comprise a second sub-band signal;

wherein the processing unit is configured to determine the threshold for the second sub-band signal based on a relation: $P\_TH\_2 = (P_{lim} - P_1)/(K-1)$; and wherein $P\_TH\_2$ is the threshold for the second sub-band signal, and $P_1$ is the signal strength parameter for the first sub-band signal.

15. The hearing protection device according to claim 14, wherein the hearing protection device is configured to keep power levels for second ones of the sub-band signals as unchanged.

16. The hearing protection device according to claim 15, wherein for the first ones of the sub-band signals for which the respective powers are reduced to the same level, the signal strength parameters respectively for the first ones of the sub-band signals are respectively above the thresholds respectively for the first ones of the sub-band signals.

17. The hearing protection device according to claim 16, wherein for the second ones of the sub-band signals remaining unchanged, the signal strength parameters respectively for the second ones of the sub-band signals are respectively below the thresholds respectively for the second ones of the sub-band signals.

18. The hearing protection device according to claim 14, wherein the sub-band signals comprise a third sub-band signal;

wherein the processing unit is configured to determine the threshold for the third sub-band signal based on a relation: $P\_TH\_3 = (P_{lim} - P_1 - P_2)/(K-2)$; and wherein $P\_TH\_3$ is the threshold for the third sub-band signal, and $P_2$ is the signal strength parameter for the second sub-band signal.

\* \* \* \* \*